United States Patent [19]

Deeds

[11] Patent Number: 5,524,755

[45] Date of Patent: Jun. 11, 1996

[54] STERILIZATION CONTAINER

[76] Inventor: Charles D. Deeds, 212 E. Park St., Auburndale, Fla. 33823

[21] Appl. No.: 447,260

[22] Filed: May 22, 1995

Related U.S. Application Data

[63] Continuation-in-part of Ser. No. 19,951, Mar. 14, 1994.

[51] Int. Cl.[6] .................................................. A61L 2/26
[52] U.S. Cl. ..................................... 206/370; 206/439
[58] Field of Search ................................ 206/439, 438, 206/370, 363, 210; 422/292, 295, 297, 300

[56] References Cited

U.S. PATENT DOCUMENTS

| | | | |
|---|---|---|---|
| 4,752,453 | 6/1988 | Nichols | 206/439 X |
| 5,183,643 | 2/1993 | Nichols | 206/439 X |
| 5,307,985 | 5/1994 | Beizermann | 206/439 X |

*Primary Examiner*—Jacob K. Ackun
*Attorney, Agent, or Firm*—George A. Bode

[57] ABSTRACT

A sterilization container for medical instruments comprising a closure having upper and lower members sealingly fastened together. Apertures are provided in the upper portion of the closure and a layer of material overlaps the apertures on the inside of the upper member so that under selected heat and humidity conditions vapors are allowed to pass through the apertures and the paper but under lower heat and humidity conditions the paper is dry and prevents the passage of vapor therethrough.

13 Claims, 4 Drawing Sheets

5,524,755

STERILIZATION CONTAINER

This application is a continuation-in-part application of a previous application by the same inventor bearing U.S. Ser. No. 29/019,951 filed Mar. 14, 1994.

This application is not, however, a continuation-in-part application of a previous application by the same inventor bearing U.S. Ser. No. 08/213,220 filed Mar. 14, 1994; however, the entire previous application Ser. No. 08/213,220 is incorporated herein by reference as if set forth in full below.

BACKGROUND OF THE INVENTION

1. Field of the Invention

The apparatus of the present invention relates to sterilization containers for use in operating rooms of hospitals and other medical uses where sterilization is required.

2. General Background

Conventional hospital procedure places medical instruments for use in operating rooms in containers which are then placed in an "autoclave" which is a chamber in which critical temperature and humidity are obtained for a critical period of time to sterilize the instruments. The chamber is evacuated under a vacuum and the sterilized instruments, which are normally in a wrapping, are removed to storage until needed for use in the operating room or other section of the hospital.

The apparatus of the present invention provides a sterilization container with an improved fastening means, improved sealing means and improved visual sterilization indicator.

SUMMARY OF THE INVENTION

A sterilization container for medical instruments providing a closure having upper and lower members sealingly fastened together. Apertures are provided in the upper member of the closure and a removable plate having apertures therein snaps onto an annular collar provided integrally on the underside of the upper member and surrounding the apertures in the upper member to securely position a layer of material between the apertures of the upper member of the closure and the plate. The layer of material between the apertures of the upper member and the plate under temperature and humidity conditions achieved only during sterilization, allows vapors to pass through the sets of apertures and the material, but, under ambient temperature and humidity conditions the material is dry and prevents the passage of vapors therethrough.

BRIEF DESCRIPTION OF THE DRAWING

For a further understanding of the nature and objects of the present invention, reference should be had to the following description taken in conjunction with the accompanying drawing in which like parts are given like reference numerals and, wherein.

DETAILED DESCRIPTION OF THE PREFERRED EMBODIMENT

Figure 1:
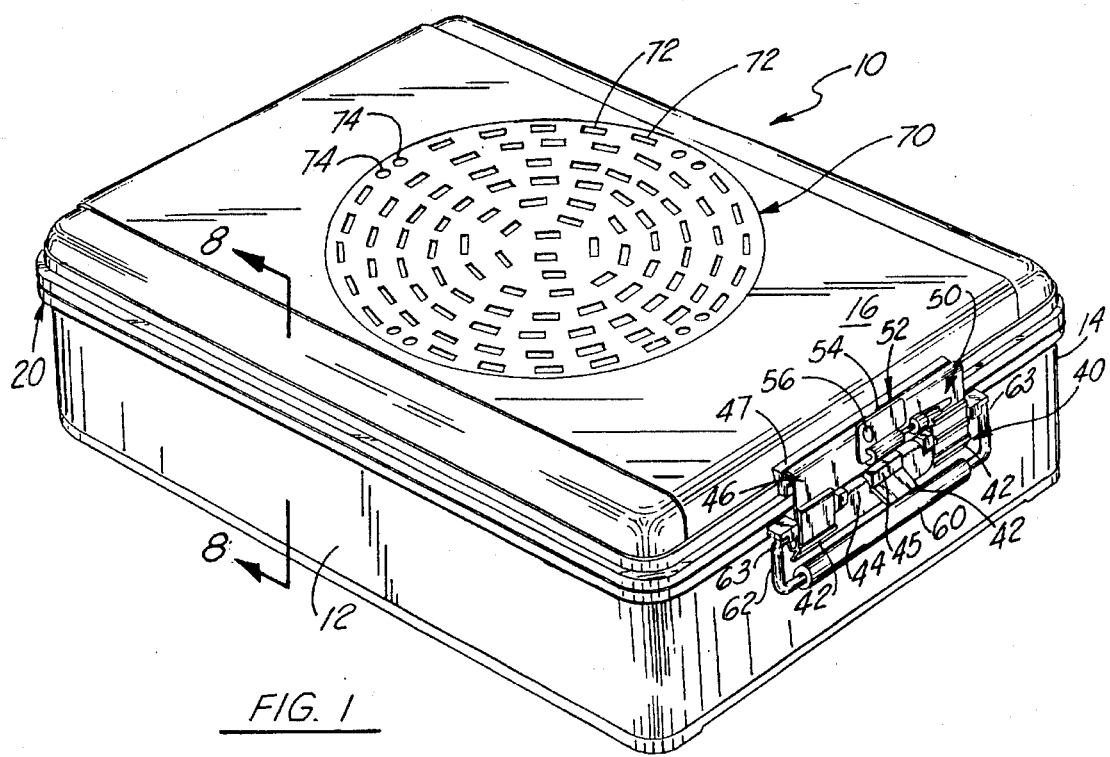
FIG. 1 is a top, front and left side perspective view of the preferred embodiment of the apparatus of the present invention.
Figure 3:
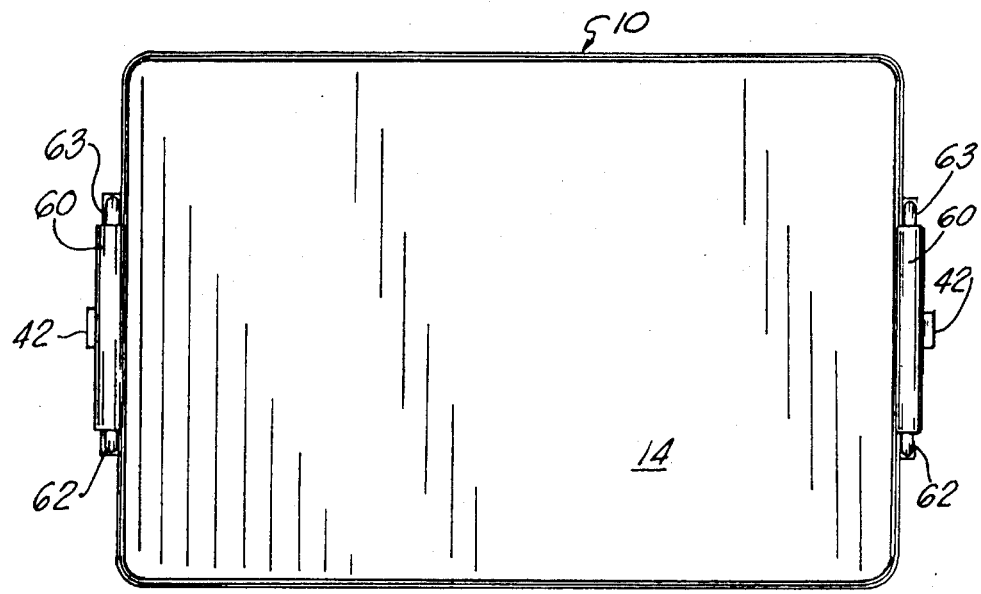
FIG. 3 is a bottom plan view of the embodiment of FIG. 1.
Figure 4:
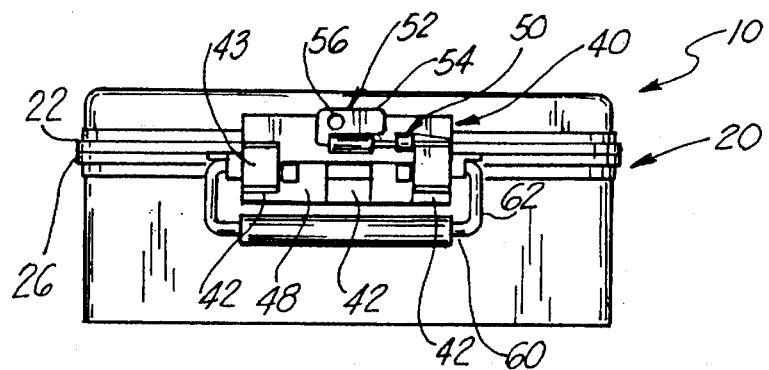
FIG. 4 is a front elevational view of the embodiment of FIG. 1, the rear elevational view being a mirror of that shown.
Figure 5:
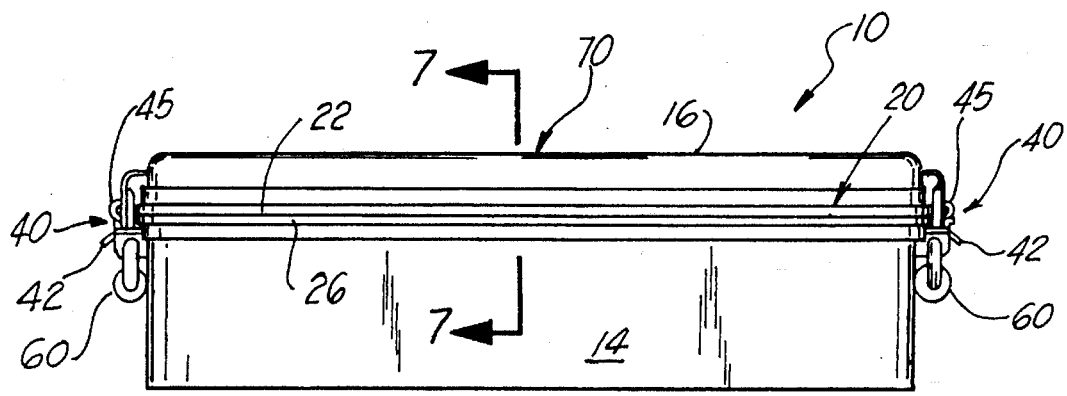
FIG. 5 is a right side elevational view of the embodiment of FIG. 1, the side opposite being a mirror of that shown.

Referring now to the drawing, and in particular FIGS. 1–5, sterilization container 10 comprises a closure 12 having bottom member or base 14 and a top or cover or lid 16. These members are preferably spring stainless steel. The lid 16 sealingly mates with bottom 14 at sealing means 20, best seen in FIG. 8 and described further herein. Sterilization container 10 has a plurality of fastening means 40 mounted on the front and rear near sealing means 20 and these fastening means 40 are best seen in FIGS. 1, 4 and 5 and are described further herein. Fastening means 40 has mounted thereon a means 50 for indicating the integrity of sealed container 10 and a means 52 for indicating that container 10 has reached terminal sterilization, as best seen in FIGS. 1 and 4. Sterilization container 10 further comprises a means 70 for allowing the steam or sterilizing vapors into container 10 for sterilizing the instruments therein, best seen in FIGS. 1, 2, 6 and 7 and described further herein.

Figure 8:
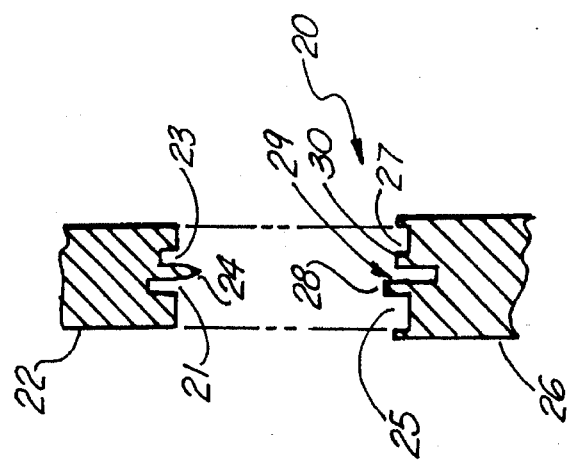
FIG. 8 is a partial cross-sectional view taken along LINES 8—8 of FIG. 1.

Referring now to FIGS. 1, 4, 5 and 8, the bottom 14 and top 16 of chamber 12 which forms sterilization container 10 is sealed by means 20. Means 20 comprises mating portions 22, 26 which form the edges of the side members of lid 16 and base 14, respectively. As best seen in FIG. 8, side portion 22 of lid 16 has at its marginal edge slots or notches 21, 23 which define protrusion or tooth 24. The marginal edge of side 26 of bottom 14 has a plurality of slots or notches 25, 29, 27 which define protrusions or teeth 28, 30. When lid or top 16 is closed onto bottom 14, the marginal edges of sides 22, 26 mate by having tooth 24 snugly fit into recess 29 and teeth 28, 30 snugly fitting into recesses 21, 23, respectively. Further, there is provided an extrudable gasket 33, best seen in FIG. 6, between the edges of side portions 22, 26 so that the sealing upon closure is air-tight. The gasket is preferably a silicone gasket which is removable and replaceable.

As best seen in FIGS. 1, 4 and 5, sterilization container 10 has its top or lid 16 removably fastened to bottom 14 by a plurality of fastener means 40. Fastener means 40 are connected to the bottom 14 and lid 16 as will be described herein and can be placed at selected locations on any side or front or rear of sterilization container 10. In the preferred embodiment, as shown in FIGS. 1–5, two such fastener means 40 are provided and they are provided at the front and rear of chamber 12, although such fasteners may be provided on either or both sides of chamber 12 or in a plurality of positions on the front, rear or sides of chamber 12. Fastener means 40 comprise plates 47 fixedly connected to bottom 14 and top 16, respectively. The connection can be by integral molding, welding or other conventional means. To upper plate 47 on lid 16 is mounted member 46 which has curled edge 44. This edge 44 accepts a plurality of conventional spring-loaded fasteners 42 which have claws 45 which engage the curled portion 44 of plate 46 and thereby fastens bottom 14 and lid 16. In the preferred embodiment, there are three (3) such fasteners 42 although more or less can be employed.

Also, provided at each fastener means 40 is a handle 62. Handle 62 has U-shaped end portions which fit at end 63 into a slot in fastener means 40 for connection thereto. A pad 60 in the form of a hollow cylindrical member can be placed over handle 62 for the comfort of the user. Also, padding 60 can be color coordinated to be an indicator of the type of instruments contained in sterilization container 10 (color indication of the instruments in sterilization container 10 can also be provided in alternate ways such as putting the color indication on the face 43 of fasteners 42). In this way, the user has a ready indication of the types of instruments that have been sterilized and are in sterilization container 10.

As best seen in FIGS. 1 and 4, the sterilization container 10 has mounted on fastener means 40 means 50 for indicating whether fastener means 40 has been unfastened after sterilization. Means 50 comprises a plastic piece in the shape of an arrow. Which upon unfastening of fastener 42 will splinter or break indicating a possible contamination of the instruments in sterilization container 10. This plastic arrow then when it is intact is an indication that sterilization container 10 has not been opened since it left an autoclave wherein the instruments were sterilized (this process will be described further herein).

Also, mounted on fastener means 40 is a means 52 for indicating the terminal sterilization of sterilization container 10. Means 52 comprises a plate 54 connected by some conventional means (such as welding, riveting or screw to fastener means 40). The plate has a small hole within which is placed chemically treated paper 56. This chemically treated paper 56 contains an ink which changes color when the proper parameters of temperature, time and humidity accomplish the terminal sterilization desired. (This chemically treated paper functions in much the same manner at litmus paper.)

Figure 2:
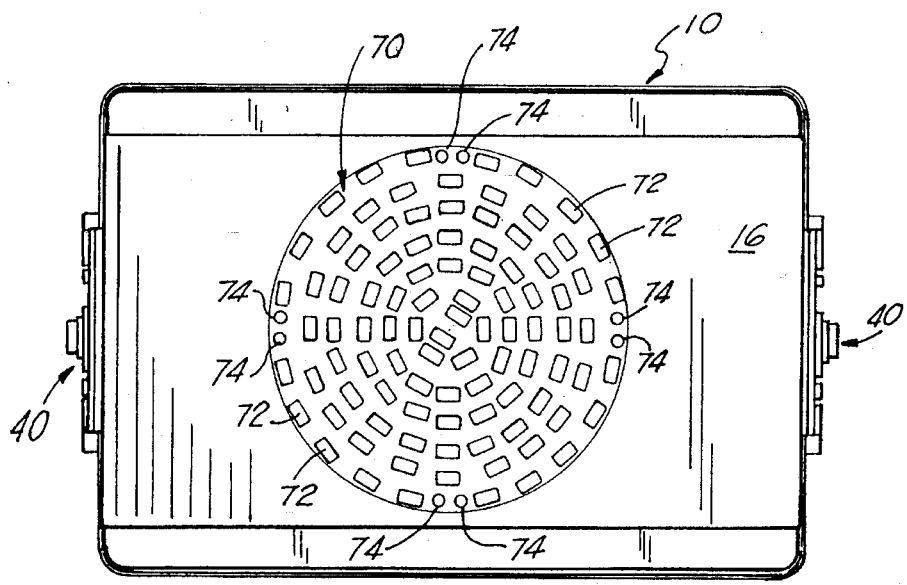
FIG. 2 is a top plan view of the embodiment of FIG. 1.
Figure 6:
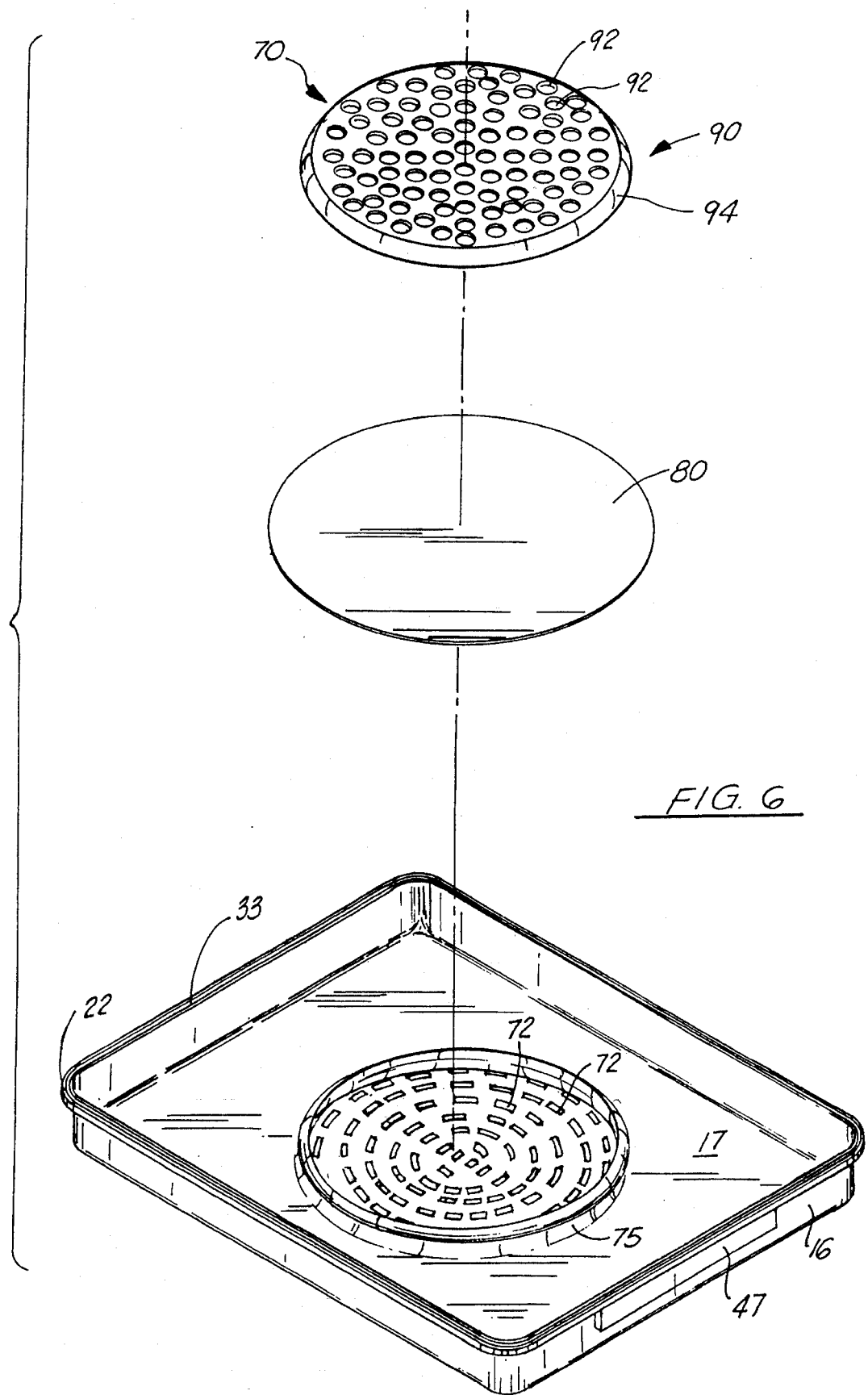
FIG. 6 is an exploded view of the cover or lid of the preferred embodiment of FIG. 1.
Figure 7:
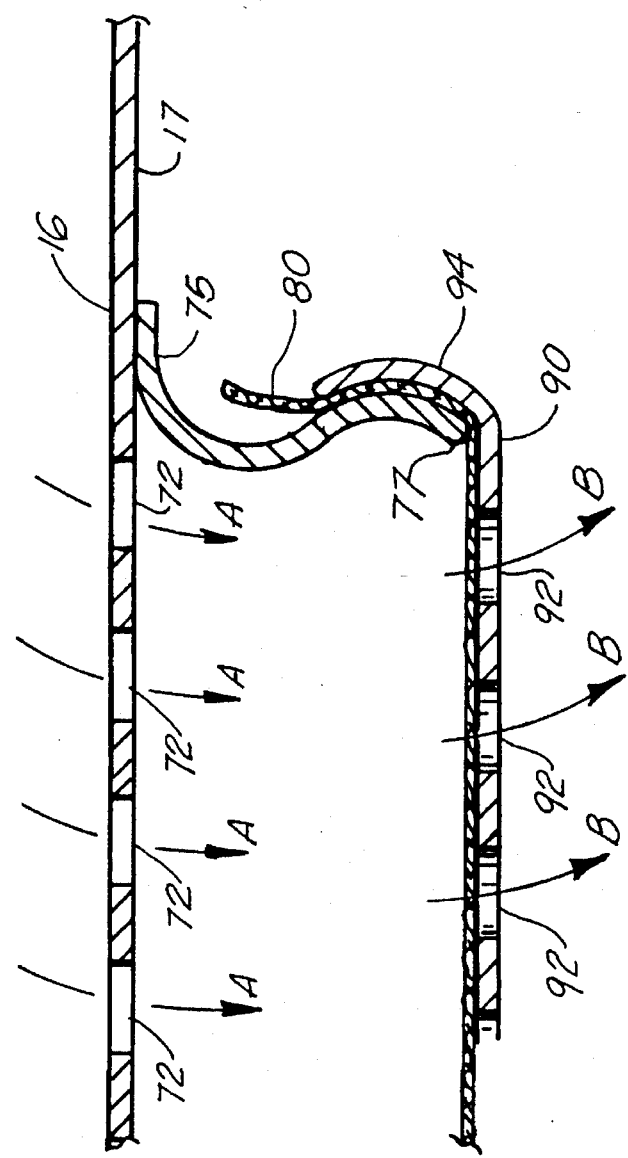
FIG. 7 is a partial cross-sectional view taken along LINES 7—7 of FIG. 5.

As best seen in FIGS. 1, 2, 6 and 7, sterilization container 10 has provided in its lid 16 a means 70 for allowing sterilization of the instruments contained therein during sterilization conditions in an autoclave (one means 70 is shown, but several may be provided depending on the size of sterilization container 10). As best seen in FIGS. 1 and 2, means 70 comprises a plurality of lances or apertures 72, 74 placed in a pattern through lid 16 (while the rectangular 72 and circular-shaped 74 apertures are shown in the preferred embodiment, other shapes can be used). As best seen in FIG. 6, the underside 17 of lid 16 has upwardly (in FIG. 6, thus downwardly in normal use) projecting collar 75 of means 70. Further, as best seen in FIG. 7, collar 75 takes a slight "S" shape bending in and then bowing out and bending in again before it reaches its terminus at point 77. Collar or projection 75 is integrally formed with surface 17 of lid 16 (such as by integral molding or welding). Further, as best seen in FIGS. 6 and 7, a disposable paper filter 80 is placed over collar 75. Such a paper is disposable and has pores which open as heat and humidity are increased from ambient conditions in an autoclave. Suitable paper may be SPUN-GUARD™ (phonetic) such as made by Kimberly-Clark. This paper has characteristics that when it is treated with heat and humidity, it allows the vapors to pass into chamber 12 through and when it dries it seals itself. With paper 80 mounted on collar 75 so that it overlaps in the manner shown in FIG. 7, a mounting plate 90 snaps onto collar 75 and secures the paper in the taught position shown in FIG. 7. Mounting plate 90 has a plurality of lances or apertures 92 therein and has an annular collar 94 sized to snap over collar 75. The apertures 92 should not align with apertures 72, 74 when means 70 is assembled.

With sterilization container 10 having paper 80 and plate 90 properly mounted as illustrated in FIG. 7 and with indicating paper 56 proper mounted in means 52 and with a second piece of such paper 56 placed within fastened and sealed chamber 12 with the instruments to be sterilized therein, the entire sterilization container 10 is placed in an autoclave (not shown). As described above, the autoclave is a conventional device used in a hospital for sterilization and provides proper parameters of temperature and humidity for a selected time to reach a desired sterilization condition (also known as "terminal sterilization"). After the necessary time period for terminal sterilization, the vapor that provides the temperature and humidity is evacuated under a vacuum and the sterilization container 10 is then removed and stored for selected use in the operating room or other location. In the autoclave, the disposable paper 80 becomes wet due to the heat and humidity of the autoclave and also porous. This allows the vapors to enter (ARROWS A and B of FIG. 7) sterilization container 10 and sterilize the instruments placed therein. When the autoclave is under a vacuum, the vapors are drawn out, the paper 80 then eventually dries and creates a seal at means 70. This in conjunction with sealing means 20 and fasteners 40 provides an effective, air-tight sterilization container 10 containing the now sterilized instruments. During the sterilization process in the autoclave, paper 56 has changed colors to indicate "terminal sterilization." The paper 56 in means 52 indicates that sterilization container 10 has been sterilized and the second portion of sterilization paper (not shown) that was placed in the sterilization container 10 also changed color due to the heat and humidity conditions in the autoclave indicating sterilization of instruments in sterilization container 10. Additionally, portions of such paper 56 can be used in the apertures 72 or 74 of means 70 for an indication to the user. Thus, when sterilization container 10 is removed from the autoclave, the color on padding 62 of handle 60 on fastener 42 of fastener means 40 indicates the type of instruments stored therein; the paper 56 indicates the existence of terminal sterilization of the sterilization container 10 and a means 50 indicates the integrity of the fastening of sterilization container 10. Upon opening of fastener means 40 means 50 will break and within sterilization container 10 should be sterilized instruments so indicated by chemical paper 56 therein.

Because many varying and differing embodiments may be made within the scope of the inventive concept herein taught and because many modifications may be made in the embodiment herein detailed in accordance with the descriptive requirement of the law, it is to be understood that the details herein are to be interpreted as illustrative and not in a limiting sense.

What is claimed as invention is:

1. A sterilization container for medical instruments comprising:

(a) a closure having upper and lower members;

(b) means for fastening into engagement said upper and lower members;

(c) means for sealing the engagement of said upper and lower members; and, (d) means for selectively allowing entry of sterilizing vapors into said sealed and fastened closure, said means comprising:

i. a plurality of apertures provided in said upper member;

ii. an annular collar secured to the inside of said upper member and surrounding said apertures in said upper member, said annular collar having a first portion bending inwardly proximate said upper member and a second portion bowing outwardly at its mid-region and a third portion bending inwardly furthest from said upper member;

iii. a plate member provided with apertures therein and adapted to snugly mount over said second and third portions of said collar; and, iv. a layer of material sealingly positioned over said collar and thereby between said plate member and said upper member when said plate member is mounted over said collar, said material under temperature and humidity conditions achieved only during sterilization, allows said sterilizing vapors to pass therethrough, but under ambient temperature and humidity conditions is dry and thereby prevents the passage of vapors therethrough.

2. The container of claim 1, further comprising means for indicating the sterilization of said closure.

3. The container of claim 2, further comprising means for indicating the continuing integrity of the fastening of said upper and lower members to form said closure.

4. The container of claim 1, wherein said apertures in said upper member and said apertures in said plate member are not in alignment when said plate member is mounted over said collar.

5. The container of the claim 1, wherein said means for sealing comprises a gasket extruded between mating marginal edges of said upper and lower members of said closure.

6. A sterilization container for medical instruments comprising:

(a) a closure having upper and lower members, said members having marginal side edges;

(b) means for fastening into engagement said marginal side edges of said upper and lower members;

(c) means for sealing the engagement of said upper and lower members;

(d) means for selectively allowing entry of sterilizing vapors into said sealed and fastened closure, said means comprising:

i. a plurality of apertures provided in said upper member;

ii. an annular collar secured to the inside of said upper member and surrounding said apertures in said upper member, said annular collar having a first portion bending inwardly proximate said upper member and a second portion bowing outwardly at its mid-region and a third portion bending inwardly furthest from said upper member;

iii. a plate member provided with apertures therein and adapted at the perimeter thereof to snugly mount over said second and third portions of said collar; and, iv. a layer of material sealingly positioned over said collar and thereby between said plate member and said upper member when said plate member is mounted over said collar, said material under temperature and humidity conditions achieved only during sterilization, allows said sterilizing vapors to pass therethrough, but under ambient temperature and humidity conditions is dry and thereby prevents the passage of vapors therethrough; and, (e) means for indicating the sterilized condition of said closure.

7. The container of claim 6, further comprising means for indicating the continuing integrity of the fastening of said upper and lower members to form said closure.

8. The container of claim 6, wherein said apertures in said upper member and said apertures in said plate member are not in alignment when said plate member is mounted over said collar.

9. The container of the claim 6, wherein said means for sealing comprises a gasket extruded between said marginal side edges of said upper and lower members of said closure.

10. A sterilization container for medical instruments comprising:

(a) a closure having upper and lower members, said members having marginal side edges;

(b) means for fastening into engagement said marginal side edges of said upper and lower members;

(c) means for sealing the engagement of said upper and lower members comprising a gasket extruded between said marginal edges of said upper and lower members of said closure; and, (d) means for selectively allowing entry of sterilizing vapors into said sealed and fastened closure, said means comprising:

i. a plurality of apertures provided in said upper member;

ii. an annular collar secured to the inside of said upper member and surrounding said apertures in said upper member, said annular collar having a first portion bending inwardly proximate said upper member and a second portion bowing outwardly at its mid-region and a third portion bending inwardly furthest from said upper member;

iii. a substantially circular plate member provided with apertures therein and adapted at the perimeter thereof to snap onto and thereby mount over said second and third portions of said collar, said apertures in said upper member and said apertures in said plate member being not in alignment when said plate member is mounted over said collar; and, iv. a layer of material sealingly positioned over said collar and thereby between said plate member and said upper member when said plate member is mounted over said collar, said material under temperature and humidity conditions achieved only during sterilization, allows said sterilizing vapors to pass therethrough, but under ambient temperature and humidity conditions is dry and thereby prevents the passage of vapors therethrough.

11. The container of claim 10, further comprising means for indicating the sterilized condition of said closure.

12. The container of claim 11, further comprising means for indicating the continuing integrity of the fastening of said upper and lower members to form said closure.

13. The container of claim 10, wherein said gasket is comprised of silicone.

\* \* \* \* \*